United States Patent [19]

Emery

[11] Patent Number: 4,744,352
[45] Date of Patent: May 17, 1988

[54] ARTIFICIAL INSEMINATION SEMEN COLLECTION PHANTOM

[76] Inventor: Joseph B. Emery, 15083 E. "C" Ave., Augusta, Mich. 49012

[21] Appl. No.: 4,550

[22] Filed: Jan. 16, 1987

[51] Int. Cl.[4] .............................................. A61F 5/00
[52] U.S. Cl. ................................. 128/79; 604/DIG. 1
[58] Field of Search .................... 128/79; 272/64, 52.5, 272/53, 103; 248/157, 423, 396; 119/1; 604/DIG. 1, 346, 347, 349-353

[56] References Cited

U.S. PATENT DOCUMENTS

| 88,432 | 3/1869 | Aifworth. | |
|---|---|---|---|
| 2,132,226 | 10/1938 | Wahlberg | 35/17 |
| 2,846,810 | 8/1958 | Ouy | 46/123 |
| 3,309,791 | 3/1967 | Kelley et al. | 35/1 |
| 3,433,477 | 3/1969 | Roberts | 272/64 |
| 4,312,350 | 1/1982 | Doan | 128/276 |
| 4,620,531 | 11/1986 | Dyer | 168/79 |

FOREIGN PATENT DOCUMENTS

| 737759 | 9/1955 | United Kingdom | 272/64 |
|---|---|---|---|
| 1087131 | 4/1984 | U.S.S.R. | 604/DIG. 1 |

OTHER PUBLICATIONS

Brochure, "Catalog 7" Lane Manufacturing Inc., Denver, Colo. 80222, pp. 9 and 10.
Normal and Abnormal Sexual Behavior, Pickett et al., 1981, p. 25.

Primary Examiner—C. Fred Rosenbaum
Assistant Examiner—J. L. Kruter
Attorney, Agent, or Firm—Henderson & Sturm

[57] ABSTRACT

An artificial vagina releaseably attached to one end of a phantom mare. The phantom includes a body section that is adjustable such that the vertical height and angle of inclination can be set to accommodate stallions of all sizes. The body section also includes a recessed area to simulate the shape and size of a mare's body and to provide the stallion with a gripping area. The phantom of the present invention makes collection more natural for the stallion and will be less work for the handler.

5 Claims, 2 Drawing Sheets

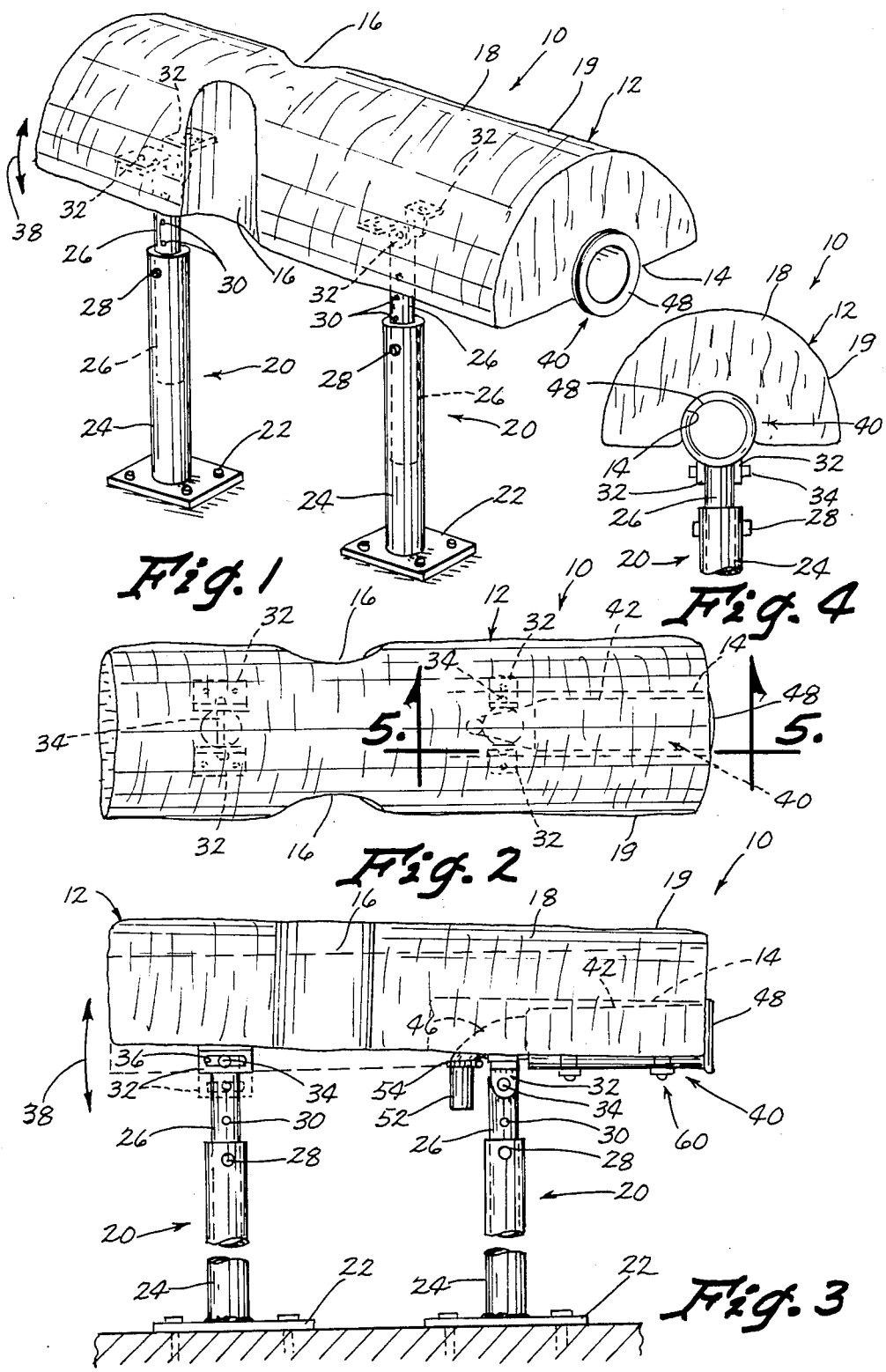

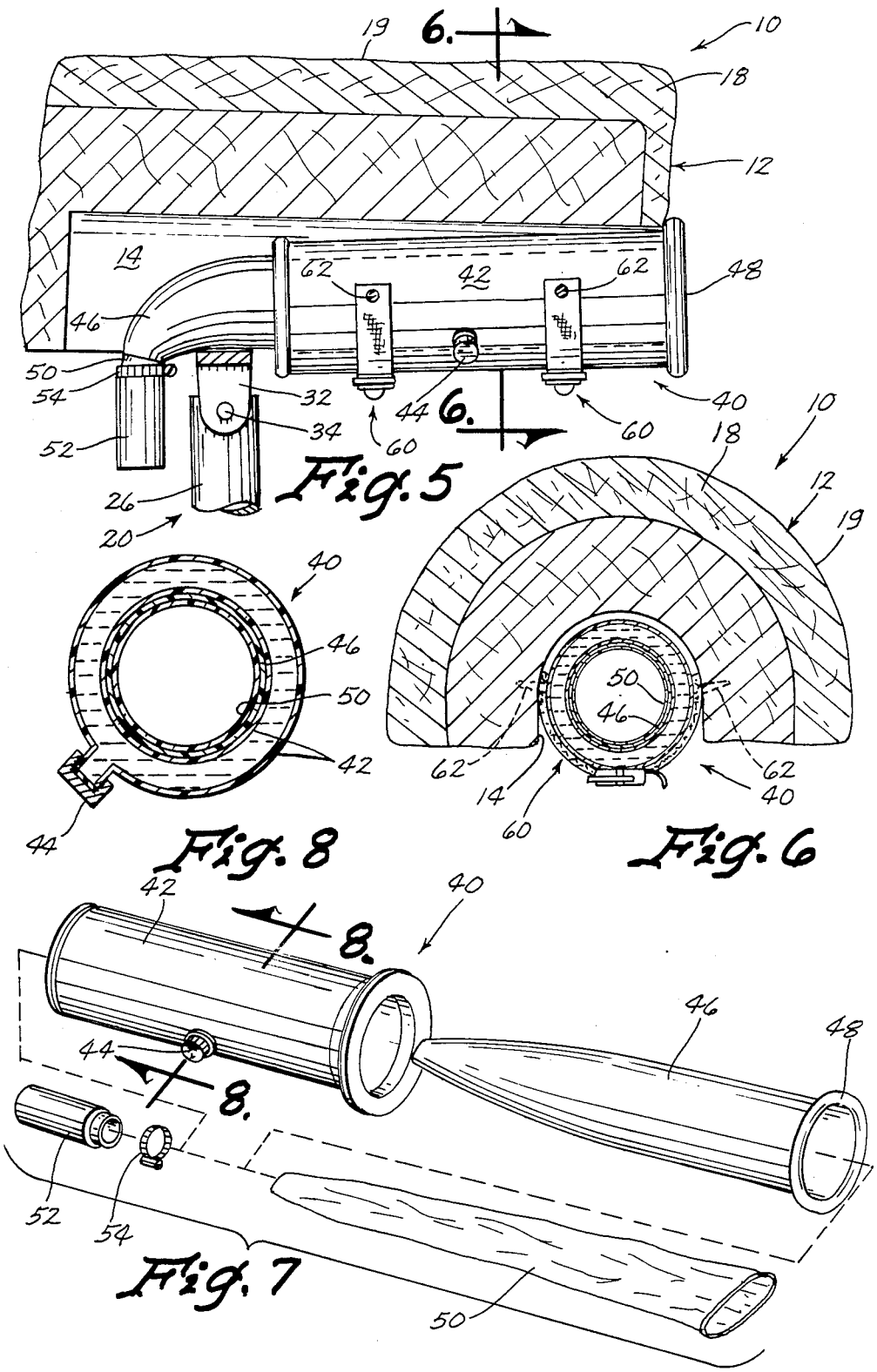

– 4,744,352 –

ARTIFICIAL INSEMINATION SEMEN COLLECTION PHANTOM

TECHNICAL FIELD

This invention relates to artificial insemination devices, and more particularly to a device used to collect semen from stallions.

BACKGROUND ART

Collection of semen from stallions for artificial insemination are taken manually into an artificial vagina. The stallion is taught to mount and breed a phantom or dummy mare and the penis is deflected to one side of the phantom into a manually held artificial vagina. Collection by this method is unnatural for the stallion and requires the efforts of a handler, as well as an assistant.

Those concerned with these and other problems recognize the need for an improved semen collection phantom for stallions.

DISCLOSURE OF THE INVENTION

The present invention provides an artificial vagina releaseably attached to one end of a phantom mare. The phantom includes a body section that is adjustable such that the vertical height and angle of inclination can be set to accommodate stallions of all sizes. The body section also includes a recessed area to simulate the shape and size of a mare's body and to provide the stallion with a gripping area. The phantom of the present invention makes collection more natural for the stallion and will be less work for the handler.

An object of the present invention is the provision of an improved artificial insemination semen collection phantom.

Another object is to provide a phantom that allows collections to easily be made by a single handler.

A further object of the invention is the provision of a phantom that is safe and lessens the risk of injury to both the stallion and the handler.

Still another object is to provide a phantom that is readily adjustable to many heights and angles to accommodate stallions of various sizes.

A still further object of the present invention is the provision of a phantom that is more natural for the stallion to mount and maintain his position during the semen collection process.

BRIEF DESCRIPTION OF THE DRAWINGS

These and other attributes of the invention will become more clear upon a thorough study of the following description of the best mode for carrying out the invention, particularly when reviewed in conjunction with the drawings, wherein:

FIG. 1 is a perspective view of the artificial insemination semen collection phantom showing the body section supported on adjustable legs, and showing the artificial vagina releasably attached to one end of the body section;

FIG. 2 is a top plan view of the body section showing in dashed line the position of the support legs and the artificial vagina;

FIG. 3 is a side elevational view illustrating the vertical and angular adjustment of the body section and showing the position of the artificial vagina in dashed line;

FIG. 4 is a partial end elevational view showing the position of the artificial vagina;

FIG. 5 is an enlarged sectional view taken along line 5—5 of FIG. 2;

FIG. 6 is a sectional view taken along line 6—6 of FIG. 5;

FIG. 7 is an exploded perspective view showing the orientation of the components of one embodiment of an artificial vagina used in conjunction with the body section; and FIG. 8 is an enlarged sectional view taken along line 8—8 of FIG. 7.

BEST MODE FOR CARRYING OUT THE INVENTION

Referring now to the drawings, wherein like reference numerals designate identical or corresponding parts throughout the several views, FIG. 1 shows the artificial insemination semen collection phantom (10) of the present invention. The collection phantom (10) includes a body section (12) having an opening (14) in one end and a recessed gripping area (16) intermediate its ends. The body section (12) is covered by a padding member (18) that in turn is covered by a washable and removable cover (19) having a smooth surface that is easily sanitized.

As best shown in FIGS. 1, 3 and 4, the body section is supported by a pair of vertically adjustable legs (20). Each leg (20) includes a floor plate (22) which supports a large tubular section (24). A small tubular section (26) is telescopically received in the large section (24) and vertical adjustment is provided by insertion of pin (28) in one of the registerable openings (30). A bracket (32) is attached to the body section (12) and a pivot pin (34) connects the bracket (32) and the top of the small tubular section (26). As shown in FIG. 3., an elongated slot (36) is provided in one of the brackets (32) to allow for angular adjustment of the body section (12) as illustrated by the directional arrow (38).

An artificial vagina (40) is releasably and adjustably attached in the opening (14) by a pair of adjustable buckle closures (60). The ends of each buckle closure (60) are attached to the body section (12) by fasteners (62) as shown in FIGS. 5 and 6. The buckle closures (60) are adjustable in length and therefore provide for angular adjustment of the artificial vagina with respect to the body section (12).

FIG. 7 illustrates one embodiment of an artificial vagina (40) that can be used in conjunction with the body section (12). The artificial vagina (40) includes a jacketed cylinder (42) that carries a fluid to maintain the device at the desired temperature. A fill cap (44) allows the emptying or refilling of the cylinder (42) with fluid. An open-ended rubber liner (46) including an enlarged lip (48) is inserted in the cylinder (42) and an open-ended plastic bag (50) is inserted within the liner (46). As best shown in FIG. 5, one end of the liner (46) and one end of the plastic bag (50) extend out of the jacketed cylinder (42), and the end of the plastic bag (50) is attached to a collection bottle (52) by clamp (54). It is to be understood that an artificial vagina other than the embodiment shown herein could be used with the body section (12).

In operation, the height and angle of the body section (12) is adjusted for the stallion. By finding each stallion's preferred position on the phantom (10), it can be properly adjusted before each collection session. Also, the angle of the artificial vagina (40) is adjusted by adjustment of the buckle closures (60). The artificial vagina (40) is thus maintained in a generally horizontal position so that semen will go to the collection bottle (52) and will not flow out of the front. Collections can be made by a single handler. After collection, the cover (19) and the artificial vagina (40) are removed and sterilized, the body section (12) and padding member (18) are sterilized, a new cover (19) and artificial vagina (40) are attached, and collection from the next stallion is started.

Thus, it can be seen that at least all of the stated objectives have been achieved.

Obviously, many modifications and variations of the present invention are possible in light of the above teachings. It is therefore to be understood that, within the scope of the appended claims, the invention may be practised otherwise than as specifically described.

I claim:

1. An artificial insemination semen collection phantom, comprising:
   a body section, said body section having an opening in one end, forming an artificial vagina and further including recessed gripping areas disposed intermediate its ends;
   a pair of vertically adjustable support leg means pivotally attached to said body section; wherein, one of the support means has a pivotal attachment which is laterally translatable with respect to said body section, and each of said support legs being vertically adjustable independent of the other support leg such that both vertical and angular adjustment of the body section relative to the ground is provided; and
   an artificial vagina releasably attached within said opening in one end of said body section.

2. The collection phantom of claim 1 further including means for adjusting the angular relationship of said artificial vagina relative to said body section.

3. The collection phantom of claim 2 wherein said means for adjusting comprises a pair of adjustable buckle closures attached to said body section.

4. The collection phantom of claim 1 wherein a padding member is disposed over said body section.

5. The collection phantom of claim 4 wherein said padding member includes a smooth surface that is easily sanitized.

* * * * *